(12) United States Patent
Steiner et al.

(10) Patent No.: US 8,669,064 B2
(45) Date of Patent: Mar. 11, 2014

(54) PROCESS FOR PROVIDING ETHANOL FROM PLANT MATERIAL

(75) Inventors: Manfred Steiner, Aubonne (CH); Ulrich Dreier, Font (CH); Ralph Beckers, Wezembeek-Oppem (BE); Walter Steiner, Aubonne (CH)

(73) Assignee: Syngenta Participations AG, Basel (CH)

( * ) Notice: Subject to any disclaimer, the term of this patent is extended or adjusted under 35 U.S.C. 154(b) by 624 days.

(21) Appl. No.: 12/743,142

(22) PCT Filed: Nov. 18, 2008

(86) PCT No.: PCT/EP2008/009734
§ 371 (c)(1),
(2), (4) Date: Aug. 30, 2010

(87) PCT Pub. No.: WO2009/062751
PCT Pub. Date: May 22, 2009

(65) Prior Publication Data
US 2011/0020891 A1   Jan. 27, 2011

(30) Foreign Application Priority Data
Nov. 16, 2007 (EP) ..................................... 07022262

(51) Int. Cl.
*G01N 33/53* (2006.01)
(52) U.S. Cl.
USPC ............................... 435/7.2; 435/41; 435/161
(58) Field of Classification Search
USPC ............................................ 435/7.2, 41, 161
See application file for complete search history.

(56) References Cited
U.S. PATENT DOCUMENTS
4,333,611 A   6/1982   Zucker et al.

FOREIGN PATENT DOCUMENTS

| | | |
|---|---|---|
| DE | 3150314 A1 | 7/1983 |
| EP | 1 978 086 A1 | 10/2008 |
| WO | 2007009463 A2 | 1/2007 |
| WO | WO 2007017200 A2 * | 2/2007 |

OTHER PUBLICATIONS

Oosterveld et al. "Arabinose and ferulic acid rich pectic polysaccharides extracted from sugar beet pulp", Carbohydrate Research, 1996, 288:143-153.*
Judelson "Operation of the autoclaves", 2004, pp. 1-7.*
Sutton et al. "Fermentation of sugarbeet pulp for ethanol production using bioengineered *Klebsiella oxytoca* strain P2", J of Sugar Beet Research, 2001, 38(1):19-34.*
Trebbi et al. "Fluorometric sucrose evaluation for sugar beet", J. Agric. Food Chem., 2004, 52:6862-6867.*
Westermann et al. "The biorefinery for production of multiple biofuels", Biofuels for Fuel Cells, 2005, Chaper 11:194-205.*
Machine translation of WO2007017200A2, pp. 1-17.*
Parr Instrument Company, "Cell Disruption Bombs—Cell Disruption by nitrogen decompression", [Online] (Nov. 4, 2002) URL: http//www.parrinst.com/doc_library/members/Parrcell.pdf, [retrieved on Apr. 22, 2008] the whole document.

* cited by examiner

Primary Examiner — Bin Shen
(74) Attorney, Agent, or Firm — Dale Skalla (57) ABSTRACT

The presently disclosed subject matter relates to processes that comprise the vacuum extrusion of plant materials. In some embodiments, the plant materials are subjected to a change in pressure of −3 kPa or more. The vacuum extrusion can be used to break open the cell walls of the plant material and of any undesirable micro-organisms associated with the plant material. In some embodiments, the vacuum extrusion can be used as a step in a process for producing ethanol from plant materials, such as from sugar beets. In some embodiments, the vacuum extrusion can be used in a process for providing a desired plant cell-derived molecule, such as a sugar or starch.

8 Claims, 3 Drawing Sheets

PROCESS FOR PROVIDING ETHANOL FROM PLANT MATERIAL

CROSS-REFERENCE TO RELATED APPLICATIONS

This application is a national phase application of International Application No. PCT/EP2008/009734, filed Nov. 18, 2008, which claims priority to European Application No. 0702226.5, filed Nov. 16, 2007.

TECHNICAL FIELD

The presently disclosed subject matter relates to processes comprising the processing (transformation) of plant materials via vacuum extrusion. The processed (transformed) plant materials can be used in processes such as anaerobic or aerobic fermentation, for example, for producing ethanol or in processes for isolating molecules, such as sugars or starches, from plant cells.

BACKGROUND

Plant cells contain many useful molecules, such as sugars and starches. Plant-derived sugars and starches are used in the food industry, for example, as sweeteners or as thickening agents. Plant-derived sugars and starches are also increasingly being used as starting materials in the production of renewable liquid fuels (i.e., biofuels), including methanol, ethanol, and butanol.

Generally, plant materials are subjected to numerous pre-treatment steps in order to facilitate the extraction of the useful molecules from the intact plant cell. For example, when sugar beets (i.e., *Beta vulgaris*) are used as a biofuel starting material or as a source of sucrose (i.e., table sugar), conventional pre-treatment steps include washing the beets to remove soil and micro-organism contaminants, such as the bacteria originating from the soil in which the beets were grown. The washed beets are then chipped or sliced in conventional cutting machines. The resulting sliced or chipped beets are scalded in hot water (i.e., between about 70° C. and about 75° C.). During this procedure, the beet cell walls are thermally denatured such that the cell walls are disrupted and become permeable to the sucrose molecules. A sucrose-containing juice is then obtained by extraction of the scalded beet material at temperatures of approximately 68° C. to 70° C.

A substantial amount of added water is needed to make the above-described extraction effective. Further, significant energy costs are accrued to effect the heating needed for both the thermal denaturation of the chipped or sliced beets and the full extraction of the juice.

Given for example the increasing importance of plant-derived ethanol, improvements to the conventional process are highly desirable. For example, processes that simplify the pre-fermentation or pre-extraction handling of sugar- and starch-containing plant materials are needed to reduce the cost, the water and/or energy usage, and the time requirements associated with conventional processes. Also of interest are improved processes that lead to an increase in the yield of products, such as alcohol, obtained from a given amount of raw plant material.

SUMMARY

The problems as described above are solved by the subject matter of the present invention as outlined below.

In one aspect the present invention provides a process for providing an extruded brei, wherein the process comprises: providing a plant material comprising intact plant cells; and vacuum extruding the plant material to break open the intact plant cells to provide an extruded brei.

In one embodiment this process comprises the additional step of pressing the plant material provided in the first step of the process at an increased pressure to provide a compressed plant material, which is then subjected to vacuum extrusion.

In some embodiments, the vacuum extruding step comprises subjecting the plant material to a reduction in pressure of about 3 kPa or more. In some embodiments, the reduction in pressure is between about 3 kPa and about 100 kPa. In some embodiments, the vacuum extruding comprises introducing the plant material to a vacuum chamber and operating the vacuum chamber at up to about a total vacuum. In some embodiments, the vacuum chamber is operated at between about 90% and about 99% vacuum. In some embodiments, the vacuum extruding step comprises: pressing the plant material to provide a compressed plant material at an increased pressure; and decompressing the compressed plant material by reducing the pressure by about 3 kPa or more.

In some embodiments, the plant material is derived from is derived from a plant selected from the group consisting of sorghum (milo), sweet sorghum, oats, barley, wheat, rye, millet, berry, grape, rye, maize, rice, potato, sweet potato, cassava, sugar beet, sugar cane, pineapple, grasses and trees.

In a preferred embodiment, the plant material is derived from sugar beet.

In some embodiments, the plant material is mashed or crushed prior to the vacuum extruding. In some embodiments, the plant material is plant material that has already been subjected to conventional sugar extraction treatments. In some embodiments, the plant material is not heated prior to the vacuum extruding. In some embodiments, the plant material is heated to between about 70° C. and about 90° C. prior to the vacuum extruding.

In some embodiments, the plant material comprises micro-organism contaminants and the process damages one or more of the micro-organism contaminants, thereby providing an extruded brei comprising fewer micro-organism contaminants than the plant material. In some embodiments, the extruded brei comprises about 1000 times fewer micro-organism contaminants than the plant material.

In a further aspect the present invention is directed to the extruded brei as obtained by the vacuum extrusion process of the present invention.

Another aspect of the present invention is directed to the use of the extruded brei or the liquid phase extracted thereof or the solid subject matter contained in said extruded brei in aerobic or anaerobic fermentation for the production of one or more biofuel(s) such as ethanol, biogas and/or biodiesel, or in the extraction of saccharides or other plant materials such as starch, cellulose, hemicellulose, pectins, proteins, enzymes.

In some embodiments, the fermentation comprises: mixing the extruded brei with water and yeast to form a fermentation mixture; and maintaining the fermentation mixture at a temperature ranging between about 18° C. and about 40° C. for a period of time. In some embodiments, the temperature ranges between about 25° C. and about 35° C. In some embodiments, the temperature ranges between about 33° C. and about 35° C. In some embodiments, the period of time ranges between about 5 hours and about 120 hours.

In some embodiments, the period of time ranges between about 10 hours and about 72 hours. In some embodiments, the period of time is about 48 hours or less.

In some embodiments, the fermentation step further comprising a liquefaction step, a saccharification step, or a combination thereof carried before the fermentation step. In some embodiments, the mixing step further comprises adding one or more enzymes to the extruded brei. In some embodiments, the mixing step further comprises adding about 25 g of a mannanase enzyme per hectoliter of extruded brei. In some embodiments, the mixing step is free of adding an enzyme.

In some embodiments, the fermenting step comprises a continuous fermentation. In some embodiments, the fermenting step comprises batch fermentation. In some embodiments, the residual fermented mixture obtained after extraction of ethanol is introduced into a biogas reactor and used as a fuel to produce energy. In some embodiments, the distillation is performed using energy produced from a biogas reactor.

Another aspect of the present invention is directed to the use of a vacuum tank or a vacuum chamber for the preparation of the extruded brei according to the present invention.

Further, the present invention is directed to a multi-step process for the subsequent production of ethanol and biogas out of plant material, wherein the process comprises: providing a plant material comprising plant cells as feedstock; subjecting said feedstock to the vacuum extrusion process of the present invention to provide an extruded brei; optionally extracting plant substances and/or metabolites other than sugars and/or starch from the brei; subjecting the complete obtained extruded brei or portions thereof to aerobic fermentation in a batch process or as a continuous process in a fermentor to provide a fermented mixture, wherein the fermented mixture comprises ethanol; separating the solid organic matter contained in the obtained fermented mixture from the liquid phase and isolating the ethanol from the liquid phase using a distiller; and using the obtained solid organic matter as a fuel for anaerobic fermentation in a biogas reactor to produce biogas or as a feed additive for livestock, or as a fertilizer; wherein the distillation and/or the separation of the liquid phase from the residual solid matter and/or the separation of the ethanol from the liquid phase using a distiller is performed using energy produced from a biogas reactor, and wherein the liquid separated from the residual solid matter and/or any aqueous effluents from the process is used as water for irrigation, cooling systems, or any other suitable use, such as in the preparation of new fermentation mixtures.

In some embodiments, the presently disclosed subject matter provides a process for producing ethanol, wherein the process comprises: providing a plant material comprising intact plant cells; vacuum extruding the plant material to break open the intact plant cells to provide an extruded brei; and fermenting the extruded brei to provide a fermented mixture, wherein the fermented mixture comprises ethanol.

In some embodiments, the fermented mixture comprises at least 9.5% ethanol, calculated based on the volume of the extruded brei. In some embodiments, the fermented mixture comprises at least 10% ethanol, calculated based on the volume of the extruded brei.

In some embodiments, the process comprises one or more steps selected from a liquefaction step, a saccharification step, or a combination thereof.

In some embodiments, about 100% of the fermented mixture is subjected to distillation to separate the ethanol from the fermented mixture, thereby providing a residual fermented mixture. In some embodiments, the residual fermented mixture is introduced into a biogas reactor and used to produce energy. In some embodiments, the distillation is performed using energy from a biogas reactor.

In some embodiments, at least about 19% more ethanol is produced than by a conventional plant-to-ethanol process, wherein the conventional process is performed in the absence of a vacuum extruding step. In some embodiments, about 25% more ethanol is produced than by a conventional process.

In some embodiments, the presently disclosed subject matter provides ethanol, wherein the ethanol is produced according to a process comprising vacuum extruding a plant material. In some embodiments, the presently disclosed subject matter provides a fuel mixture, wherein the fuel mixture comprises ethanol produced according to a process comprising vacuum extruding a plant material.

In some embodiments, the presently disclosed subject matter is directed to a process for providing a saccharide, the process comprising: providing a plant material comprising intact plant cells and vacuum extruding the plant material to provide an extruded brei, wherein the extruded brei comprises a saccharide.

In some embodiments, the saccharide comprises a sugar, a starch, or a combination thereof. In some embodiments, the saccharide comprises sucrose.

In some embodiments, the presently disclosed subject matter provides a saccharide, wherein the saccharide is provided according to a process comprising vacuum extruding a plant material.

It is an object of the presently disclosed subject matter to provide a process for producing ethanol or for providing a saccharide from plant materials, wherein the process comprises vacuum extruding the plant material.

An object of the presently disclosed subject matter having been stated hereinabove, and which is achieved in whole or in part by the presently disclosed subject matter, other objects will become evident as the description proceeds when taken in connection with the accompanying drawings as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art. Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

1. DEFINITIONS

Following long-standing patent law convention, the terms "a" and "an" mean "one or more" when used in this application, including the claims. Thus, "an enzyme" or "a plant material" can refer to a plurality (i.e., two or more) enzymes or plant materials.

As used herein, the term "about" modifying any amount can refer to the variation in that amount encountered in real world conditions of producing sugars and ethanol, e.g., in the lab, pilot plant, or production facility. Unless otherwise indicated, all numbers expressing quantities of percentage, temperature, time, pH, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the phrase "plant material" refers to all or part of any plant material that comprises sugars, starches, and/or other molecules that can be broken down into sugars and/or starches. The plant material can be derived from a grain, fruit, legume, seed, stalk, wood, vegetable, root, or a part thereof. The plant material can be obtained from a plant selected from the group consisting of oats, barley, wheat, berry, grape, rye, maize (i.e., corn, including sweetcorn), rice, potato, sugar beet (including all *Beta vulgaris* ssp.), sugar cane, pineapple, grasses and trees. Thus, suitable plant material includes grains such as corn, sorghum (milo), sweet sorghum, barley, wheat, rye, rice, and millet; and root crops, tubers, or roots such as sugar beet, potato, sweet potato and cassava. The plant material can be a mixture of such materials and by-products of such materials, e.g., corn fiber, corn cobs, stover, or other cellulose- and hemicellulose-containing materials, such as wood or plant residues. Generally, the term "plant material" refers to a relatively unprocessed plant material, having intact plant cells.

The term "saccharide" refers to a carbohydrate monomer, oligomer or larger polymer. Thus, a saccharide can be a compound that includes one or more cyclized monomer unit based upon an open chain form of a compound having the chemical structure $H(CHOH)_nC(=O)(CHOH)_mH$, wherein the sum of n+m is an integer between 2 and 8. In some embodiments, each cyclized monomer unit is based on a compound having a chemical structure wherein n+m is 4 or 5. Thus, saccharides can include monosaccharides including, but not limited to, aldohexoses, aldopentoses, ketohexoses, and ketopentoses such as arabinose, lyxose, ribose, xylose, ribulose, xylulose, allose, altrose, galactose, glucose, gulose, idose, mannose, talose, fructose, psicose, sorbose, and tagatose, and to hetero- and homopolymers thereof. Saccharides can also include disaccharides including, but not limited to sucrose, maltose, lactose, trehalose, and cellobiose, as well as hetero- and homopolymers thereof.

As used herein the term "sugar" refers to fermentable monosaccharides disaccharides, and trisaccharides, particularly to mono- and disaccharides. Thus, sugars include, but are not limited to, sucrose, fructose, glucose, galactose, maltose, lactose, and mannose.

As used herein the term "starch" refers to a polymer of glucose containing $\alpha(1-4)$ and $\alpha(1-6)$ glycosidic bonds. In particular, starch refers to a mixture of amylose and amylopectin.

The term "cellulose" refers to a polysaccharide of β-glucose comprising β-(1-4) glycosidic bonds.

The term "dextrin" refers to a linear, water-soluble oligomer of $\alpha$-(1-4)-D-glucose. Dextrins can be prepared from the hydrolysis of starch.

The term "biofuel" refers to a fuel that is derived from biomass, i.e., a living or recently living biological organism, such as a plant or an animal waste. Biofuels include, but are not limited to, biodiesel, biohydrogen, biogas, biomass-derived dimethylfuran (DMF), and the like. In particular, the term "biofuel" can be used to refer to plant-derived alcohols, such as ethanol, methanol, propanol, or butanol, which can be denatured, if desired prior to use. The term "biofuel" can also be used to refer to fuel mixtures comprising plant-derived fuels, such as alcohol/gasoline mixtures (i.e., gasohols). Gasohols can comprise any desired percentage of plant-derived alcohol (i.e., about 10%, 15%, 20%, 25%, 30%, 35%, 40%, 45%, 50%, 55%, 60%, 65%, 70%, 75%, 80%, 85%, 90%, or 95% plant-derived alcohol). For example, one useful biofuel-based mixture is E85, which comprises 85% ethanol and 15% gasoline.

The terms "transform," "transforming," "processing" and variations thereof are used herein to refer to processes of treating generally intact plant cells such that molecules of interest therein (e.g., starches, sugars, proteins, etc) can be easily accessed (e.g., extracted or fermented). When applied to a molecule, the term "transform" and variations thereof, refer to the conversion of one molecule to another, such as the enzyme-catalyzed transformation of glucose to fructose or to the hydrolysis of an oligosaccharide into a smaller (i.e., shorter chain length) oligosaccharide or sugar.

The term "brei" refers to a pulp or mash prepared from a plant tissue. The term "extruded brei" refers to a pulp or mash of plant material that has been vacuum extruded and in which some, most, or, more preferably, all of the plant cells are no longer intact.

The term "feedstock" as used herein can refer to a generally unprocessed plant (i.e., a plant material) that can be used as the source of a desired product or as the source of a starting material for preparing a desired product. A feedstock can be used to prepare a brei which can subsequently be fermented. The feedstock can comprise a harvested, sometimes defoliated plant that has not been chopped, sliced or washed. Desired feedstock products include starches; sugars; cellulose; hemicellulose; pectins; and fermentation products, including, but not limited to alcohols; and fermentation by-products, such as solid stillage, which can include both plant-derived solids and yeast-derived solids, and which can be used as an animal feed or as a fuel source for biogas reactors. Desired feedstock products can also include the energy from a biogas reactor.

The term "fermentation mixture" refers to a mixture of brei (e.g., extruded brei) comprising a plant-derived, fermentable molecule (e.g., a sugar) and an aqueous component, which can include, for example, water, de-ionized water, a process water (i.e., backset, steam, condensate), or any combination thereof. The fermentation mixture can also include a microorganism (e.g. yeast), nutrients (e.g., yeast nutrients), a pH-adjusting compound (e.g., a salt), and, in some embodiments, one or more enzymes. For example, in fermentation mixtures wherein a sugar is to be fermented into alcohol, the mixture can include one or more enzymes to process a plant-derived sugar or to process any starches present in the brei (e.g., to perform saccharification)

The term "enzyme" refers to a compound (e.g., a protein) that catalyzes the conversion of one molecule into another. The term "enzyme" as used herein includes any enzyme that can catalyze the transformation of a saccharide or cellulose molecule. For example, enzymes include starch-degrading or isomerizing enzymes including, for example, α-amylase, endo or exo-1,4- or 1,6-α-D-glucoamylase, glucose isomerase, β-amylases, α-glucosidases, and other exo-amylases; starch debranching enzymes, such as isoamylase, pullulanase, neo-pullulanase, iso-pullulanase, amylopullulanase and the like; glycosyl transferases such as cyclodextrin glycosyltransferase and the like; cellulases such as exo-1,4-β-cellobiohydrolase, exo-1,3-β-D-glucanase, hemicellulase, β-glucosidase and the like; endoglucanases such as endo-1,3-β-glucanase and endo-1,4-β-glucanase and the like; L-arabinases, such as endo-1,5-α-L-arabinase, α-arabinosidases and the like; galactanases such as endo-1,4-β-D-galactanase, endo-1,3-β-D-galactanase, 1-galactosidase, α-galactosidase and the like; mannanases, such as endo-1,4-β-D-mannanase, β-mannosidase, α-mannosidase and the like; xylanases, such as endo-1,4-1-xylanase, β-D-xylosidase, 1,3-β-D-xylanase, and the like; and pectinases. In some embodiments, the enzyme comprises a mixture of a mannanase, a cellulase, and a glucosidase. In some embodiments, the enzyme is a mannanase.

For use in a process of the presently disclosed subject matter, an enzyme can be specifically selected based on the specific end product desired from the extruded brei. The enzyme can also be selected to provide a desired property to the extruded brei or fermentation mixture. For example, an enzyme can be selected in order to produce a desired viscosity in the fermentation mixture.

Starch-derived end products can have various chain lengths based on the extent of processing or on various branching patterns desired. For example, an α-amylase, glucoamylase, or amylopullulanase can be used under short incubation times to produce longer chain polymer products and under longer incubation times to produce shorter chain products or sugars. A pullulanase can be used to specifically hydrolyze branch points in the starch yielding a high-amylose starch, or a neopullulanase can be used to produce starch with stretches of α-1,4 linkages with interspersed α-1,6 linkages. Glucosidases can be used to produce limit dextrins, or a combination of different enzymes can be used to make other starch derivatives. In some embodiments, a glucose-isomerase can be selected to convert glucose into fructose.

In particular, α-amylase refers to an enzyme which cleaves or hydrolyzes internal α (1-4) glycosidic bonds in starch to produce α 1-2 bonds and result in smaller molecular weight oligosaccharides. These smaller molecular weight oligosaccharides include, but are not limited to, maltose, which is a disaccharide; maltotriose, a trisaccharide; malto-tetrose, a tetrasaccharide; and other oligosaccharides. The enzyme α-amylase (EC 3.2.1.1) can also be referred to as 1,4-α-D-glucan glucanohydrolase or glycogenase. A variety of α-amylases are known in the art and are commercially available. An α-amylase can be from a fungal or bacterial origin and, in some embodiments, can be expressed by a transgenic plant. The α-amylase can be thermostable.

Glucoamylase (also known as amyloglucosidase) refers to the enzyme that has the systematic name 1,4-α-D-glucan glucohydrolase (E.C. 3.2.1.3). Glucoamylase removes successive glucose units from the non-reducing ends of starch. A variety of glucoamylases is known in the art and is commercially available. For example, certain glucoamylases can hydrolyze both the linear and branched glycosidic linkages of starch, amylose, and amylopectin. Glucoamylase can be from a fungal origin and can be expressed in transgenic plants. The glucoamylase can be thermostable.

The enzyme can be cellulase (E.C. 3.2.1.4), also known as an endoglucanase, which catalyzes the hydrolysis of 1,4-β-D-glycosidic linkages. The cellulase can be of microbial origin, such as derivable from a strain of a filamentous fungus (e.g., *Aspergillus, Trichoderma, Humicola, Fusarium*). Commercially available cellulase preparations which can be used include, but are not limited to, CELLUCLAST™, CELLUZYME™, CEREFLO™, and ULTRAFLO™ (available from Novozymes A/S, Bagsvaerd, Denmark), SPEZYME™ CE and SPEZYME™ CP (available from Genencor International, Inc., Rochester, N.Y., United States of America) and ROHAMENT® CL (available from AB Enzymes GmbH, Darmstadt, Germany).

The terms "glycosidic bond" and "glycosidic linkage" refer to a linkage between the hemiacetal group of a sugar and a hydroxyl group of an alcohol (which can be another sugar).

As used herein the terms "liquefaction," "liquefy," "liquefact," and variations thereof refer to the process or product of converting starch to soluble dextrinized substrates (e.g., smaller polysaccharides).

The term "secondary liquefaction" refers to a liquefaction process that takes place after an initial period of liquefaction or after a jet cooking step of a multi-stage liquefaction process. The secondary liquefaction can involve a different temperature than a previous liquefaction step or can involve the addition of additional starch-digesting enzymes (e.g., α-amylase).

As used herein, the terms "saccharification" and "saccharifying" refer to the process of converting polysaccharides to fermentable sugars using enzymes. Saccharification products are, for example, glucose and other small (low molecular weight) oligosaccharides such as monosaccharides, disaccharides, and trisaccharides.

"Fermentation" or "fermenting" can refer to the process of transforming an organic molecule into another molecule using a micro-organism. For example, "fermentation" can refer to aerobic transforming sugars or other molecules from extruded plant material to produce alcohols (e.g., ethanol, methanol, butanol); organic acids (e.g., citric acid, acetic acid, itaconic acid, lactic acid, gluconic acid); ketones (e.g., acetone), amino acids (e.g., glutamic acid); gases (e.g., $H_2$ and $CO_2$), antibiotics (e.g., penicillin and tetracycline); enzymes; vitamins (e.g., riboflavin, $B_{12}$, beta-carotene); and/or hormones. Fermentation can include fermentations used in the consumable alcohol industry (e.g., beer and wine), dairy industry (e.g., fermented dairy products), leather industry, and tobacco industry. Thus, fermentation includes alcohol fermentation. Fermentation also includes anaerobic fermentations, for example, for the production of biogas.

Fermenting can be accomplished by any organism suitable for use in a desired fermentation step, including, but not limited to, bacteria, fungi, archaea, and protists. Suitable fermenting organisms include those that can convert mono-, di-, and trisaccharides, especially glucose and maltose, or any other biomass-derived molecule, directly or indirectly to the desired fermentation product (e.g., ethanol, butanol, etc.). Suitable fermenting organisms also include those which can convert non-sugar molecules to desired fermentation products.

In some embodiments, the fermenting is effected by a fungal organism (e.g., yeast or filamentous fungi). The yeast can include strains from a *Pichia* or *Saccharomyces* species.

In some embodiments, the yeast can be *Saccharomyces cerevisiae*. In some embodiments, the fermenting is effected by bacteria. For example, the bacteria can be *Clostridium acetobutylicum* (e.g., when butanol is the desired fermentation product) or *Corynebacterium glutamicum* (e.g., when monosodium glutamate (MSG) is the desired fermentation product). In some embodiments, the micro-organism (e.g. yeast or bacteria) can be a genetically modified micro-organism. In some instances, the organism can be yeast modified to have a strong ethanol production capacity.

In certain embodiments, fermenting can comprise contacting a mixture including plant-derived sugars with yeast under conditions suitable for growth of the yeast and production of ethanol. In some embodiments, fermenting involves simultaneous saccharification and fermentation (SSF). The amount of yeast employed can be selected to effectively produce a desired amount of ethanol in a suitable time and/or upon the sugar content of a given fermentation mixture.

2. VACUUM EXTRACTION

Conventional processes for isolating valuable molecules from biological sources, such as plant cells, often involve extensive chemical, mechanical, and/or thermal steps for disrupting cell walls, such as the slicing and boiling usually required to extract sucrose-rich juice from sugar beets. Examples for mechanical treatment of plant material to break open the cell structure include friction and shearing by applying manual pressure via mortar and pestle (e.g., dry-grinding) or crushing and squeezing (e.g., grinding in a hammer mill and then placing into a screw press to separate the juice from the fibrous plant material with or without the addition of chemicals or steam to increase the yield of juice). Other proposed methods of disrupting cell walls to isolate molecules from plant cells include mechanical agitation, ultrasonic treatment, or electroporation. See, for example, U.S. Patent Application Publication No. 2006/0106210.

The presently disclosed subject matter provides processes for processing (transforming) plant materials, such as sugar- and/or starch-containing plant materials, (i.e., intact plant cells) using vacuum extraction to provide an extruded brei. The processed (transformed) plant materials can afterwards be used in processes such as anaerobic or aerobic fermentation, for example for producing ethanol, or in processes for isolating molecules, such as sugars or starches, from plant cells or the cell walls of plant cells.

In this context, it has to be noted that the terms "vacuum extraction" and "vacuum extrusion" are used interchangeably herein, both referring to the method of breaking open the cell structure of plant material by a reduction of pressure as described herein.

The brei according to the present invention is the product obtained after subjecting plant material to the vacuum extraction described and claimed herein. The brei consists of a homogenised liquid phase containing the cell debris as solid matter. Dependent on the liquid content brei has the texture of pulp or mash. In general, the size of the solid matter in the brei depends on the size of plant material subjected to vacuum extraction. The bigger the size of the plant material used as feedstock for the vacuum extraction, the bigger the particle size of the cell debris present in the extruded brei.

In general, the processing of plant materials using vacuum extrusion provides an extruded brei, wherein the solid matter is in solution (i.e. solved in the cell sap) and has a strong influence on the osmotic pressure and the redox potential of the extruded brei. The potential osmotic pressure of the extruded brei is dependent from the number and the nature of the particles being in solution. The specific osmotic pressure and redox potential of the extruded brei allows an activation of the micro-organisms during fermentation and allows for an improved use of the energy in the extruded brei resulting in improved yields in terms of, for example, ethanol or biogas.

The brei or homogenate according to the present invention has the following advantages in view of the processes known in the prior art:

in the extruded brei, former cell contents, such as sugars, starch or combinations thereof, are released from the cells (i.e. are not longer enclosed by intact structures of the intact plant cell) and can thus be easily contacted by any enzyme or micro-organism present in or added to the extruded brei;

the homogenised solid matter in the brei offers an increased surface area allowing micro-organism and/or enzymes to attach for processing same;

without wishing to be bound to any theory, it is believed that the process of vacuum extraction further results in the formation of smaller molecules by breaking up long chain molecules giving rise to improved fermentation yields;

the extruded brei will comprise fewer micro-organism contaminants than the plant material used as feedstock because the micro-organisms present in the plant materials are subjected to the same forces as the plant materials and are thus destroyed to a great extend. As a result the number of micro-organism contaminants in the extruded brei is lower than the number present in the plant material the brei is derived from;

no further chemicals (such as, for example, liquid ammonia) for treating the biomass prior to the vacuum extraction and no high pressure gases (such as, for example, nitrogen) are required resulting in a simple and more cost effective process compared to those described in the prior art; and processing of plant material using the vacuum extraction of the present invention and as described herein can further result in energy savings over conventional processes, such as those involving, for example, the boiling or heat diffusion-related extraction of sugars from plant feedstock, as well as in a reduction in the amount of water needed to process the plant material. For example, in the production of sugar out of sugar beet no preparation of raw juice or thick juice prior to the sugar extraction is necessary.

The vacuum extruding can comprise subjecting the plant material to a change in pressure ($\Delta P$) of about $-3$ kPa or more. In some embodiments, the change in pressure ranges from about $-3$ kPa to about $-100$ kPa. In some embodiments, the change in pressure is between about $-3$ kPa and about $-20$ kPa.

Thus, "vacuum extruding" (or vacuum extraction") as used herein refers to subjecting a cellular material, such as plant cells, to a reduction in pressure, thereby breaking open the cells. In some embodiments, the plant material is exposed to a vacuum. For example, the plant material can be provided to a decompression chamber wherein the decompression chamber is a vacuum chamber or a vacuum tank. The vacuum chamber or tank can be operated at up to about a total vacuum (i.e., about 100% vacuum). In some embodiments, the vacuum chamber can be operated between about 90% vacuum and about a total vacuum. In some embodiments, the vacuum chamber can be operated at between about 90% and about 99% vacuum. The plant material can be exposed to the vacuum for any amount of time sufficient for breaking open the intact plant cells. Without wishing to be bound to any theory, it is believed that subjecting the intact plant cells to a reduction in pressure, such as by exposing them to a vacuum, causes an increase in vapor pressure within the individual cells, thereby breaking open or "exploding" the cells.

In some embodiments, the plant material used as the feedstock for the vacuum extrusion is derived from a plant selected from the group consisting of a grain, a root, a vegetable, a fruit, a legume, and a grass. In some embodiments, the plant material is derived from a plant selected from the group consisting of corn, oats, rice, wheat, barley, millet, cassava, potato, sweet potato, rye, sugar beet, sugar cane, sorghum, sweet sorghum, Jerusalem artichoke, fodder beet, grape, pineapple, apple, pear, peach, and apricot. In some embodiments, the plant material is derived from sugar beet (including all *Beta vulgaris* ssp.).

The providing of plant materials for use in the vacuum extruding process can comprise defoliation of the plant material and, if desired, limited size reduction of the initial plant feedstock, such as by crushing or mashing the feedstock into chunks or pieces of plant material. In a preferred embodiment of the present invention the plant materials for use in the vacuum extruding process according to the present invention are reduced to a size of less than 20 mm, preferably to a size of less than 10 mm. In some embodiments, the plant material comprises pieces having at least one dimension between about 0.1 mm and about 5 mm, preferably of about 2-3 mm.

Generally, the size of the pieces of plant material for use in the vacuum extruding process is smaller, if plant material with lower water content is used. Thus, dry plant materials such as grains (like corn or cereals) are reduced to smaller sizes (up to the size of flour by actually milling it), whereas for plant materials with higher water content such as, for example sugar beet, a particle size of about 2 mm is sufficient. Other means to get plant material with sufficient water content is swelling of the plant material in water prior to the vacuum extrusion or the mixing with water.

In other equally preferred embodiments, however, the plant material is not mashed or crushed. For example, in some embodiments, the plant material can comprise the whole plant. Thus, the plant material can comprise whole sugar beets.

In further preferred embodiments the feedstock for the vacuum extrusion process according to the present invention is plant material that has already been subjected to conventional sugar extraction treatments such as standard liquefaction and saccharification employed in the art of sugar extraction (e.g., slicing and boiling as it is usually performed to extract sucrose-rich juice from sugar beets yielding exhausted beet slices as remnants). In general, said already processed plant material can be used in the present invention if it is in a processed state without all sugar being solubilized (i.e. the processed material contains residual sugar). Preferably, the processed material used as feedstock contains some residual water content. If not, water has to be added prior to further processing as described herein.

In some cases, a brief trench floatation step can be performed to reduce the amount of soil or rocks present in the feedstock, however such a step is not always necessary. In addition, as the vacuum extrusion can generally be done without any intensive heating (e.g., heating above 100° C.) or wetting of the plant feedstock, the presently disclosed methods can result in energy savings over conventional processes involving the boiling or heat diffusion-related extraction of sugars from plant feedstock, as well as in a reduction in the amount of water needed to process the plant material.

In some embodiments, the vacuum extrusion can comprise a first step of compressing the plant material and a second step of rapidly decompressing the compressed plant material. For example, in some embodiments, the plant material can be compressed and then introduced into a decompression chamber. The compressing can serve to homogenize the plant material or the resultant extruded brei. For instance, the compressing can serve to provide smaller or more uniformly sized pieces of plant material. Preferably, the vacuum extrusion is free of a compression step which allows a high throughput of plant material with a high degree of biomass disruption.

In some embodiments, the plant material can be heated prior to the reduction in pressure. For example, the plant material can be heated after any initial crushing of the plant material, but prior to being placed under vacuum. In embodiments wherein the plant material is vacuum extruded via a two-step compression and decompression method, the plant material can be heated either prior to compression or after compression, but before any decompression.

In general, the higher the temperature of the plant material just before the reduction in pressure, the more efficient the vacuum extrusion step can be (e.g., more plant cells are broken open in less time and/or larger sized pieces of plant material can be used). Further, heating of the plant material prior to the vacuum extrusion process also helps to reduce the number of micro-organism contaminants. In some embodiments, the plant material can be heated to a temperature as high as about 120° C. (e.g., when the plant material comprises whole sugar beets). In most embodiments, however, a temperature of as high as 120° C. is not required for efficient vacuum extrusion of the plant material. Thus, preferably, the plant material is heated to a temperature of less than about 100° C.

In some embodiments, the plant material can be heated to between about 70° C. and about 90° C. (e.g., about 70, 71, 72, 73, 74, 75, 76, 77, 78, 79, 80, 81, 82, 83, 84, 85, 86, 87, 88, 89, or 90° C.). In some embodiments, the plant material is heated to a temperature of about 70° C. or less. In embodiments using lower temperatures, the length of time the plant material is exposed to vacuum can be increased or the plant material can be provided in smaller pieces. If the plant material is provided in particularly small pieces, the plant material can be heated to a temperature of about 60° C. or less. In some embodiments, the plant material is not heated prior to vacuum extrusion. If sugar beet is uses as feedstock, the feedstock is preferably heated to 70-90° C. prior to decompression.

The decompression in the vacuum chamber results in a decrease of the temperature of the resulting brei. In general, the higher the initial temperature of the plant material is prior to decompression, the higher the temperature of the brei is after decompression. If for example sugar beet is processed for the production of ethanol, heating of the Sugar Beet plant material to a temperature of about 70° to about 90° C. is thus preferred, as decompression will result in a drop of the temperature to between 30 and 40° C. which is the ideal temperature for the fermentation of the brei and will not require further heating of the brei prior to fermentation.

If any micro-organisms are present on the plant material (e.g., from the soil in which the plant was grown or that became associated with the plant material during storage), the cell walls of the micro-organism can also be exploded during the vacuum extruding process. Thus, in some embodiments, the extruded brei will comprise fewer micro-organism contaminants than the plant material from which the extruded brei was derived. In particular, when the plant material is heated to between about 70° C. and about 90° C. prior to the vacuum extrusion step, both efficient extrusion of the plant cells and good reduction in the number of micro-organism contaminants can be achieved. For example, when the plant material is heated to about 80° C., the number of microorganisms present in the extruded brei can be about 1000 less than the number present in the plant material prior to vacuum extrusion.

Thus, in some embodiments, the number of micro-organisms present in the extruded brei can be about 10 times, 100 times, or 1000 times less than the number of micro-organisms present in the plant material prior to the vacuum extrusion. In some embodiments, the number of micro-organisms in the extruded brei can be more than 1000 times less than the number present in the plant material.

The plant material can be heated via any suitable method or using any suitable heating apparatus. Examples for heating systems that can be used in the present invention comprise, but are not limited to, for example, tube heat exchangers, multi-tube heat exchanger, and direct steam injection. In general, a heating method or apparatus that provides homogenous heating of the plant material is most desirable. For example, the plant material can be heated using a Thermocompact system (Della Toffola, S.p.A., Treviso, Italy).

Figure 1:
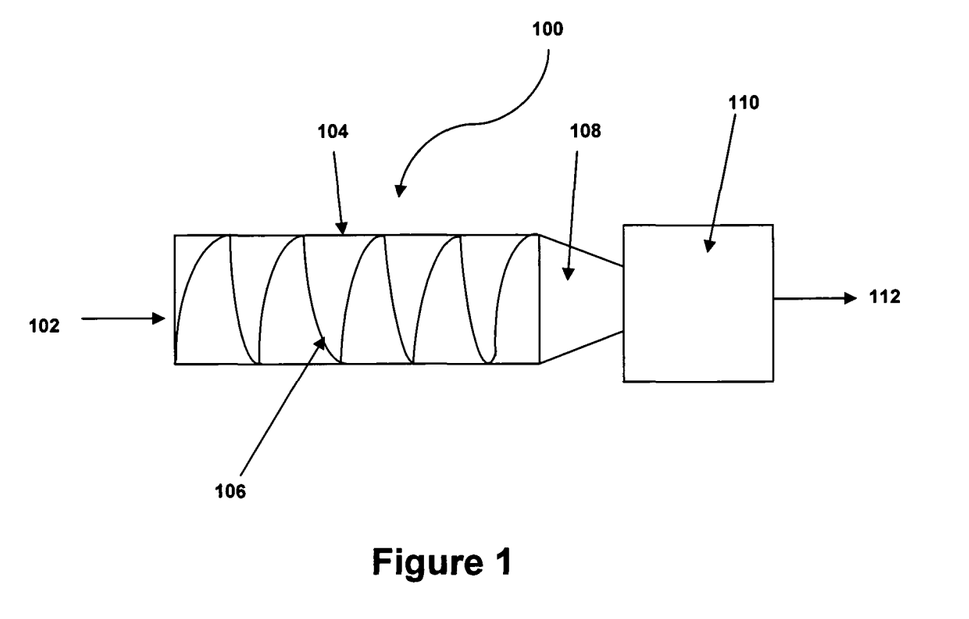
FIG. 1 is a schematic illustration of an apparatus for vacuum extruding plant materials according to the presently disclosed subject matter.

Any suitable apparatus can be used in the vacuum extrusion. For example, any commercially available vacuum tank or vacuum chamber can be used such as those apparatuses provided by Della Toffola, S.p.A., Treviso, Italy, for use in foodstuff industry. As illustrated in FIG. 1, one suitable vacuum extrusion apparatus 100 comprises screw press 104 for transporting the plant material into the vacuum tank. Other types of presses, including, but not limited to oil presses, can be used. Plant material (e.g., sugar beet chunks) is introduced at press end 102 (where, for example, the pressure can be 1000 Pa) and compressed by screw 106 into compression chamber 108. In some embodiments, the plant material is compressed until the pressure in compression chamber 108 is about three times that of the pressure at 102 (for example, to 3000 Pa). The compressed plant material in compression chamber 108 is then released into decompression chamber 110, which results in a decrease in pressure of at least 3 kPa. The extruded brei then exits the decompression chamber via outlet 112, which can include, for example, a cell wheel. Suitable decompression chambers are known to the person skilled in the art.

The brei obtained by the vacuum extrusion process of the present invention and the vacuum extrusion process as such can be used in several applications, including, but not limited to, for example, aerobic and anaerobic fermentation, the so-called "betaprocess" as well as the extraction of plant substances contained in plant cells or plant cell walls as will be described herein below.

a. Ethanol Production Process

In some embodiments, plant material transformed using vacuum extrusion can be used as a source of sugars in subsequent fermentation steps. The fermentation of a vacuum extruded brei can provide a product selected from the group consisting of an alcohol (e.g., ethanol, methanol, propanol, butanol, etc.), lactic acid, citric acid, an amino acid, fructose, propanediol, distillers dried grain (DDG), distillers dried grain and solubles (DDGS), or a combination thereof.

In some embodiments, the alcohol is ethanol. Thus, in some embodiments, the presently disclosed subject matter provides a process for producing ethanol, wherein the process comprises providing a plant material comprising intact plant cells; vacuum extruding the plant material to break open the intact plant cells to provide an extruded brei; and fermenting the extruded brei to provide a fermented mixture, wherein the fermented mixture comprises ethanol.

In some embodiments, the plant material for use in a process for producing ethanol is derived from a plant selected from the group consisting of a grain, a root, a vegetable, a fruit, a legume, and a grass. In some embodiments the plant material is derived from a plant selected from the group consisting of corn, oats, rice, wheat, barley, millet, cassava, potato, sweet potato, rye, sugar beet, sugar cane, sorghum, sweet sorghum, Jerusalem artichoke, fodder beet, grape, pineapple, apple, pear, peach, and apricot. In some preferred embodiments, the plant material is derived from a sugar beet (including all *Beta vulgaris* ssp.).

According to the presently disclosed processes, in some embodiments, the plant material is provided without any extensive washing or other cleaning steps. Thus, in some embodiments, the plant material further comprises microorganism contaminants and the vacuum extruding process serves to damage the micro-organisms such that the number of micro-organism contaminants in the extruded brei is lower than the number present in the plant material. In some embodiments, particularly in embodiments wherein the plant material is heated to between about 70° C. and about 90° C. prior to vacuum extruding, the number of micro-organism contaminants in the extruded brei is reduced by about 1, 2, 3, 4, or 5, orders of magnitude as compared to the number of micro-organisms originally present in the plant material. In some embodiments, the vacuum extruding reduces the number of micro-organism contaminants by at least about 4 orders of magnitude compared to the amount of micro-organisms originally present on the plant material. The reduction in the number of micro-organism contaminants can result in an increase in the amount of alcohol or other fermentation product produced from the fermentation of given amount of extruded brei, since there will be less micro-organisms competing with the micro-organism (e.g., yeast) specifically added to the fermentation mixture prepared from the extruded brei to effect the fermentation. Reduction in the number of micro-organism contaminants can be detected via microscopic means or can be reflected in a reduction in the amount of lactic acid produced from a fermentation mixture prepared from the extruded brei.

The presently disclosed process can be performed without slicing or otherwise cutting the plant material. In some embodiments, the plant material is provided by harvesting and defoliating the plant material. In some embodiments, it can be desirable to reduce the plant material in size prior to the vacuum extrusion. Thus, in some embodiments, the plant material is crudely crushed or mashed prior to vacuum extrusion to reduce the size of the plant material. In some embodiments, the plant material is reduced to a size of less than 20 mm, preferably to a size of less than 10 mm. In some embodiments, the plant material comprises pieces having at least one dimension between about 0.1 mm and about 5 mm, preferably of about 2-3 mm. In other embodiments, the plant material used in the presently disclosed processes can be provided without significantly reducing the plant material in size. For example, in some embodiments, the plant material can comprise whole sugar beets. In further preferred embodiments the plant material is plant material that has already been subjected to conventional extraction treatments such as standard liquefaction and saccharification employed in the art (e.g., slicing and boiling as it is usually performed to extract sucrose-rich juice from sugar beets yielding exhausted beet slices as remnants) as already described above.

In some embodiments, the harvested, defoliated plant material is stored for a period of time prior to the vacuum extruding step. For example, the plant material can be stored at normal environmental temperature and humidity (e.g., outside) for a period of time including one or more days, weeks, months, or years. Prior to the vacuum extruding step, spoiled plant material resulting from the storage conditions does not need to be separated from the other plant material provided for the vacuum extruding step.

Figure 2:
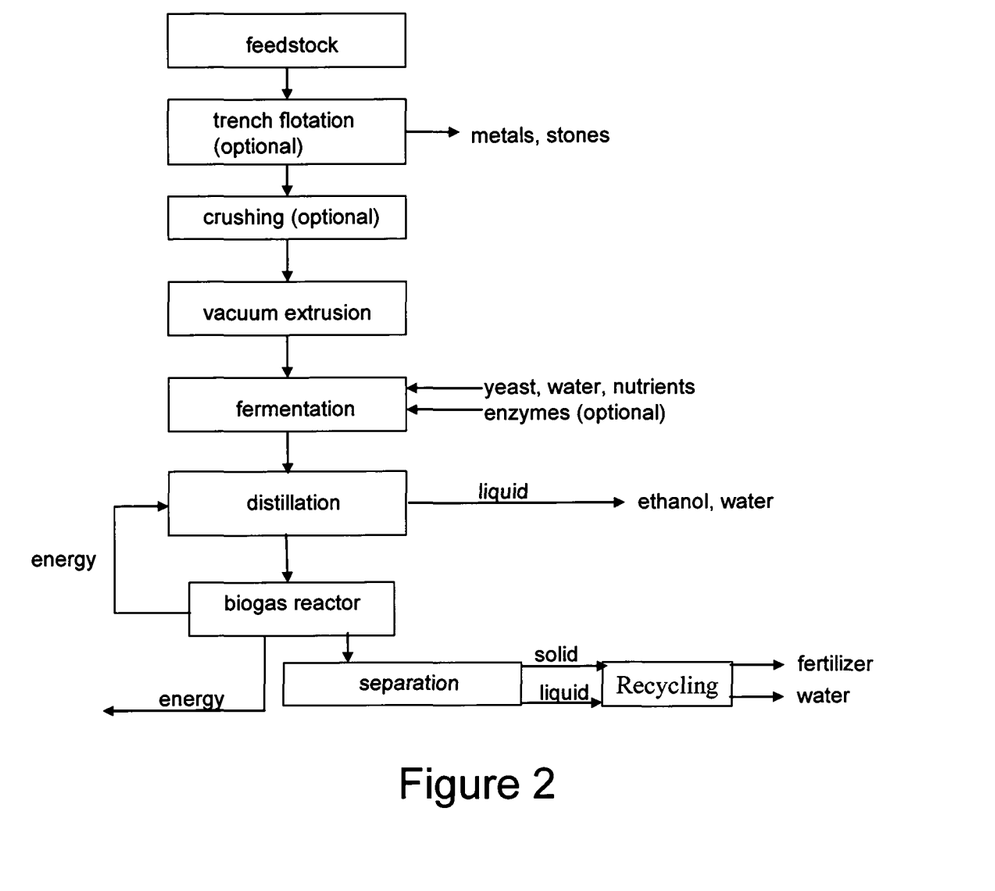
FIG. 2 is a block diagram showing a process for the production of ethanol from plant materials according to the presently disclosed subject matter wherein about 100% of the fermented mixture is subjected to a distillation step.

In some embodiments, providing the plant material can comprise a flotation step, wherein non-plant material contaminants, such as stones and metals, can be removed from the initially provided plant material (i.e., plant feedstock). During the flotation step, the plant material is floated in water in a trough or other vessel (e.g., a tank), while the non-plant contaminants fall to the bottom of the trough or other vessel. Use of a trough can also serve to convey the plant material to the machinery used in the vacuum extrusion portion of the process. If desired, such as when the plant material has been stored at a low temperature (e.g., during the winter months), the water for the flotation step can be provided at a slightly elevated temperature (i.e., 25-30° C.), in order to facilitate the crushing of the plant material prior to the vacuum extruding process. FIG. 2 illustrates a fermentation process of the presently disclosed subject matter wherein a plant feedstock is subjected to a trench flotation step.

Following the trench flotation step (if used) and any plant material size reduction step (e.g., a mashing or crushing step), the plant material is subjected to vacuum extrusion to provide an extruded brei. The vacuum extrusion can comprise subjecting the plant material to a reduction in pressure of about 3 kPa or more. In some embodiments, the plant material is subjected to a reduction in pressure of between about 3 kPa and about 100 kPa. In some embodiments, the plant material is subjected to a reduction in pressure of between about 3 kPa and about 20 kPa.

In some embodiments, the vacuum extrusion comprises exposing the plant material to an absolute vacuum. In some embodiments, the plant material can be introduced to a vacuum chamber that is operating at or can operate at about 90% vacuum up to about a total vacuum. In some embodiments, the vacuum chamber can operate at between about 90% and about 99% vacuum. In some embodiments, the vacuum extrusion comprises compression and decompression steps. Thus, in some embodiments, the presently disclosed vacuum extruding process comprises pressing the plant material to provide a compressed plant material at an increased pressure and then decompressing the compressed plant material by reducing the pressure of the compressed plant material by about 3 kPa or more. Any suitable apparatus can be used for the vacuum extrusion. For example, any commercially available vacuum tank or chamber can be used such as those apparatuses provided by Della Toffola, S.p.A., Treviso, Italy, for use in foodstuff industry.

As noted hereinabove, in some embodiments, the plant material is heated prior to the vacuum extruding. In some embodiments, the plant material is heated to a temperature of less than 100° C. In some embodiments, the plant material is heated to a temperature of between about 70° C. and about 90° C. In some embodiments, the plant material is heated to a temperature of about 70° C. or less. In some embodiments, the plant material is heated to a temperature of about 60° C. or less. In some embodiments, the plant material is provided for vacuum extrusion free of a heating step. As already noted above, any suitable method or any suitable heating apparatus can be used. Examples for heating systems that can be used in the present invention comprise, but are not limited to, for example, tube heat exchangers, multi-tube heat exchanger, and direct steam injection. In general, a heating method or apparatus that provides homogenous heating of the plant material is most desirable. For example, the plant material can be heated using a Thermocompact system (Della Toffola, S.p.A., Treviso, Italy).

In some embodiments the extruded brei comprises a sugar, a starch, or a combination thereof. In the extruded brei, the sugar, starch or combination thereof is not enclosed in an intact plant cell and, thus, can be contacted by any enzyme or micro-organism present in or added to the extruded brei. In some embodiments, the extruded brei can comprises sucrose, wherein the sucrose is free of an intact plant cell.

As shown in FIG. 2, following vacuum extrusion, the extruded brei is fermented. In general, the extruded brei can be used in aerobic and anaerobic fermentation. In some embodiments, the fermenting step comprises mixing the extruded brei with an aqueous solution (e.g., water or distillate (i.e., recovered water from a distillation process)) and yeast or other fermentation micro-organism to form a fermentation mixture. The fermentation mixture is maintained at a temperature ranging between about 18° C. and about 40° C. for a period of time. In some embodiments, the fermentation mixture is maintained at a temperature ranging between about 25° C. and about 35° C. In some embodiments, the temperature is maintained at between about 33° C. and about 35° C. (i.e., about 33° C., about 34° C., or about 35° C.). In some embodiments, the temperature is maintained for a period of time ranging between about 5 hours and about 120 hours. In some embodiments, the period of time ranges between about 10 hours to about 72 hours. In some embodiments, the period of time is about 48 hours or less. For example, the period of time can range between about 10 hours and about 48 hours. Most preferred the fermentation mixture is incubated for a period of time ranging between 10 hours and 24 h.

Although it has to be noted that the addition of one or more additional enzyme(s) is not necessary to obtain good fermentation results due to the beneficial characteristics of the extruded brei of the present invention, such an addition is nevertheless contemplated in the present application. In some embodiments, an additional enzyme or enzymes are added to the extruded brei or the fermentation mixture to hydrolyze starches therein to fermentable sugars, to further break down plant cell walls, or to otherwise transform the sugar and starch molecules present. For example, when vacuum extruded sugar beet is used to prepare a fermentation mixture, additional enzymes added to the fermentation mixture can include mannanases, glucosidases, and cellulases. In some embodiments, the additional enzyme is a mannanase, such as, but not limited to, PEKTINEX™ (Novozymes A/S, Bagsvaerd, Denmark). The mannanase or other enzymes can be used to liquefy the fermentation mixture, facilitating both the physical handling of the fermentation mixture and the conversion of the fermentation mixture to alcohol.

In some embodiments, yeast nutriments and pH adjusting chemicals are added to the fermentation mixture in order to optimize fermentation. The amount of yeast, enzyme, yeast nutriment, and pH-adjusting chemical, as well as the fermentation time and temperature can be adjusted based upon the chemical analysis of the extruded brei and/or the original plant material. The addition of yeast and any associated compounds such as the yeast nutriments, enzymes and pH adjusting chemicals, can be referred to as "inoculation." Suitable yeast nutrients include compounds with free amino nitrogens (FANs) and ammonium compounds.

In some embodiments, wherein the plant material comprises sugar beet, the inoculation comprises adding enzymes, yeast, soda, urea, sulfuric acid, phosphoric acid. Addition of the chemicals can adjust the pH of the fermentation mixture to about 5 or less.

The amount of water added can serve to keep the ethanol concentration at about 12% or lower, to keep from killing the yeast. As will be understood by one of skill in the art, the amount of chemicals added can be based on attaining a desired sucrose to N ratio. For example, soda, urea, sulfuric acid, and phosphoric acid can be added in a ratio of about 6 g soda, 3 g urea, 8 g sulfuric acid, and 2 g phosphoric acid to provide a desired sucrose to nitrogen ratio. A specific beet plant can also be selected for use in the process based upon its nitrogen or betaine content. The brei and/or fermentation mixture can be analyzed by near infrared spectroscopy (NIRS) at suitable timepoints before and during the fermentation to assess the amount of alcohol, sugars and/or other chemical components of the mixture.

In the most preferred embodiment of the present invention the extruded brei obtained from the vacuum extrusion of the present invention is directly subjected to anaerobic or aerobic fermentation without further addition of any substances.

In some embodiments, oxygen gas ($O_2$) is added to the fermentation mixture at a given time period after the fermentation process has begun. For example, in some embodiments, $O_2$ is added after the fermentation process is about two thirds complete. In some embodiments, $O_2$ is added to a target concentration of between about 8 and about 20 mg/l of fermentation mixture. In some embodiments, $O_2$ is added to a target concentration of about 15 mg/l of fermentation mixture. Higher concentrations of $O_2$ can develop the yeast instead of fermenting the sugar into ethanol. Thus, control of oxygen content can be used to insure that the highest possible amount of the available sugars are fermented and transformed into ethanol.

Figure 3:
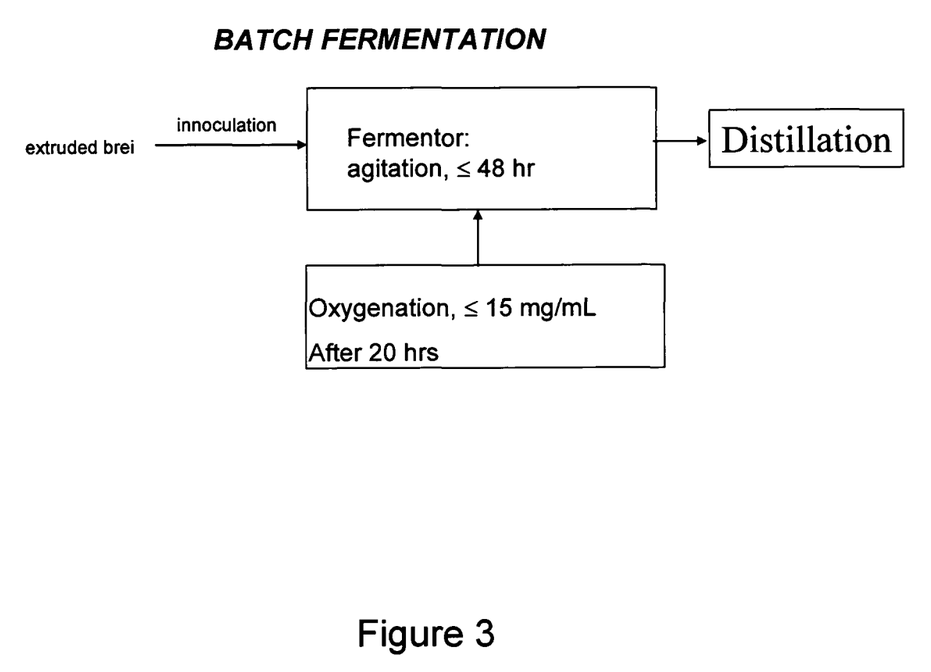
FIG. 3 is a block diagram showing a process for batch fermentation according to the presently disclosed subject matter.

The fermentation step can be run as a batch process or as a continuous process. In some embodiments, the fermentation step comprises a continuous fermentation process, wherein the fermentation mixture is moved (e.g., pumped) through a series of fermentors (e.g., tanks) to provide a sufficient time for the entire fermentation process. An example of a batch fermentation process is shown in FIG. 3. The vacuum extruded plant material (i.e., the extruded brei) can be inoculated with yeast and fermented in a suitable fermentor tank or vat for a period of time of about 48 hours or less. During fermentation, the fermentation mixture can be agitated, for example, by stirring or shaking. After the first 20 hours of fermentation, the fermentation mixture is oxygenated to a level of about 15 mg/l or less. As described further herein below, the entire fermentation mixture can then be used in a distillation step, to distill the ethanol present in the fermented mixture, separating it from other materials in the mixture. The materials remaining after the distillation of the ethanol can be referred to as the residual fermented mixture. Any suitable fermentor can be used.

In some embodiments, the fermentation process is a continuous fermentation process that comprises four fermentation steps. The inoculated extruded brei (i.e., the fermentation mixture) can be introduced into a first fermentor wherein the mixture is held without agitation for a period of time, such as for up to about 36 hours. Decantation by gravity results in the separation of mud and non-plant material from the fermentation mixture. The fermentation mixture is then moved to a second fermentor where agitation takes place. The fermentation mixture can reside in the second fermentor, for example, for up to about 48 hours. In the third fermentor, the fermentation mixture is oxygenated with $O_2$ gas up to an $O_2$ concentration of about 15 mg/l of fermentation mixture. In the fourth fermentor, final fermentation takes place. Residence time in the fourth fermentor can be for up to about 36 hours.

Preferably, the fermentation process is a batch fermentation process.

In some embodiments, such as when the plant material comprises a high starch content (e.g., when the plant material is derived from potato, cassava or a grain) or has a higher starch than sugar content, the process can comprise additional steps, such as liquefaction and/or saccharification steps. Such additional steps can be performed following the vacuum extrusion and prior to the fermentation step. For example, the process can include one or more liquefaction and/or saccharification steps prior to inoculation with yeast.

As will be understood by one of skill in the art, liquefaction and/or saccharification can be accomplished by exposing the extruded brei to a starch-degrading or other enzyme for a period of time at a desired temperature and at a desired pH. In some embodiments, the process can comprise a step wherein liquefaction of starch is accomplished by exposing the extruded brei to an α-amylase enzyme while the pH and temperature of the extruded brei is adjusted to the optimal pH and temperature for the activity of the enzyme. The pH can be adjusted to about 5.8 or another pH associated with optimal enzyme activity. The pH can be lower (i.e., less than about 5.0) when using a low-pH enzyme. The temperature can be between about 60° C. and 95° C. The time period can be for about several minutes to about several hours.

In some embodiments, starch in the extruded brei can be processed using a multi-step liquefaction process, which can comprise an initial liquefaction using an α-amylase at temperature between about 60° C. and about 95° C. for about 30 minutes to one hour, followed by a jet cooking step wherein the extruded brei is heated to between about 105° C. and about 120° C. for a period of between about 5 and about 20 minutes. The jet cooking can be followed by a secondary liquefaction step wherein additional enzyme is added and the extruded brei is heated to between about 60° C. and about 95° C. for an additional period of time, which can comprise from one to up to several hours (i.e., 2, 3, 4, or 5 hours). In some embodiments, the secondary liquefaction step comprises heating the extruded brei to between about 80° C. and about 95° C. In some embodiments, the secondary liquefaction step can comprise heating the extruded brei to between about 90° C. and about 95° C.

In some embodiments, the extruded brei is treated to a saccharification step prior to the fermentation, wherein dextrins present in the extruded brei (including those produced during a post-vacuum extrusion liquefaction step) are further hydrolyzed to produce fermentable sugars. Suitable enzymes for use in saccharification steps include, but are not limited to, glucoamylases, α-glucosidases, acid amylases, and mixtures thereof. Again the saccharification can be performed at a pH and at a temperature chosen to provide for maximal enzyme activity. In some embodiments, the saccharification is performed for a period of between several hours and one or more days (i.e., one, two or three days). In some embodiments, saccharification of the dextrins during a pre-fermentation step is only partial and the fermentation step comprises a simultaneous saccharification and fermentation (SSF) step, wherein both yeast and saccharifying enzymes are present in a fermentation mixture.

Following fermentation, whether via a continuous or batch process, the fermented mixture can be separated into a solid phase comprising solid organic matter, such as spent yeast solids and solid plant materials, and a liquid phase, comprising water and ethanol. The separation can be performed by using any suitable technique or apparatus. In some embodiments, the separation can be performed in a centrifuge or in a press. In some embodiments, the separation can be performed by filtration or decantation. The liquid and solid phases can then be further purified, if desired, to attain one or more desired end products, including the ethanol from the liquid phase and one or more additional products from the liquid and/or solid phases.

The ethanol from the fermentation mixture or from the liquid phase of the fermentation mixture can be isolated by any suitable method. In some embodiments, the ethanol is isolated by distillation. The water collected from the liquid phase can be used in the preparation of fermentation mixtures or in biogas reactors. Alternatively, the water can be further purified for any desired use, including re-entry into an environmental or civic water system. Thus, purified water from the process can be used for irrigation. Further any aqueous effluent produced as part of the plant-to-ethanol process can also be recycled and/or reused.

The solid phase material can be used, for example, as a fuel for a biogas reactor, as a feed additive for livestock, or as a fertilizer. In preferred embodiments, the solid is used as fuel for biogas reactors. In some embodiments, the solid organic matter separated from the fermented mixture can comprise a pressed cake, having a pH of about 3. Prior to use in the biogas reactor, the pH can be adjusted to between about 6 and about 8, for example to pH 7.5, with ionized water. (The residual water from the distillation process can be used for this purpose.) The resulting slurry is methanized (i.e., anaerobically, using micro-organisms). Following methanization, the residues can be pressed and/or centrifuged and separated into one phase comprising organic matter and minerals, which can further comprise proteins and can be acidified and used a fertilizer, and into a second phase comprising water, which can be demineralized by inverse osmoses.

In some embodiments, as illustrated by FIG. 2, it can be desirable for about 100% of the fermented mixture to be provided to a distillation apparatus, without any separation of solids and liquids. Thus, about the total or entire fermented mixture can be subjected to a distillation step altogether. Ethanol production methods involving distillation of ethanol from entire fermented mixtures are believed to lead to higher ethanol outputs. In preferred embodiments, the residual fermented mixture (i.e., after the distillation of alcohol and, in some embodiments, of water) is then provided as fuel to a biogas reactor. Methods that provide the residue from the distillation of an entire fermented mixture to a biogas reactor are believed to provide higher energy output from the biogas reactor than when separated components from a fermented mixture are used, because the mixture provided to the biogas reactor can comprise all of the remaining carbon from the fermentation mixture, including carbon that can be left behind when the liquid phase separated out of a fermented mixture is distilled by itself and the distillation residue is discarded.

As shown in FIG. 2, any material remaining after the residual fermented mixture is used in the biogas reactor can be separated into solids and liquids and/or recycled as desired. For example, the solids separated after use of the materials in the biogas reactor (or even the entire residue) can be used as fertilizer, while the separated liquid from the materials and/or any aqueous effluents from the process can provide water for irrigation, cooling systems, or any other suitable use, such as in the preparation of new fermentation mixtures.

In some embodiments, such as in the process illustrated in FIG. 2, the energy produced from the biogas reactor can be used to provide the energy needs required by the distillation process or in another step in the production of ethanol from plant material. Thus, in some embodiments, the presently disclosed methods for producing ethanol supply some of their own energy needs.

In some embodiments, the presently disclosed process for producing ethanol can produce more ethanol or can produce ethanol more quickly or at lower fermentation temperatures than a conventional plant-to-ethanol process. As noted hereinabove, increased ethanol production can be accomplished by using a method comprising the distillation of ethanol from the entire fermentation mixture. In addition, without being bound to any particular theory, the open cell walls believed to result from the presently disclosed vacuum extrusion processes can increase the attack region for yeast and enzymes during fermentation of the extruded brei. Thus, in some embodiments, a greater amount of the sugar available in a plant feedstock (e.g., the sugar naturally present in the plant cells prior to any starch or cellulose hydrolysis) is converted into ethanol than would be converted in a conventional plant-to-ethanol process (e.g., ethanol production from a conventionally prepared sugar beet juice). In some embodiments, the presently disclosed process results in up to 19% higher ethanol production than that produced by a conventional plant-to-ethanol process performed on the same amount of plant material in the absence of a vacuum extruding step. In some embodiments, the presently disclosed transformation process can result in up to 25% higher ethanol production compared to a conventional process. In some embodiments, fermentation of a mixture comprising an extruded brei results in production of 90% of the total amount of ethanol in the first 20 hours of fermentation.

Another aspect of the present invention further contemplates the direct use of the extruded brei as fuel for biogas reactors without subjecting it to aerobic fermentation for the production of ethanol first. For such embodiments the information given above with regard to the biogas reactors apply in a similar manner.

b. Plant Product Extraction

In some embodiments, plant material transformed using vacuum extrusion can be purified to isolate and/or extract a desired plant-derived molecule or molecules. The desired plant-derived molecule comprises, but is not limited to a saccharide, such as a sugar or a starch. Plant sources of sugar include, but are not limited to, sugar beet (including all *Beta vulgaris* ssp.), sugar cane, sweet sorghum, fruits, and fodder beets. Sources of starch include, but are not limited to grains, potato, cassava, and Jerusalem artichoke. Starches isolated from plant materials (e.g., corn, potato, cassava, etc) can be used as food additives, such as thickening agents or stabilizing agents, or in other industries, such as the adhesive, textile, or paper industry. Sugars, such as sucrose from sugar beet (including all *Beta vulgaris* ssp.), can be used as table sugar, added to other food products during manufacturing as a sweetener, or transformed into other sugars, such as glucose or fructose, which can also be used as sweeteners or nutrition supplements.

Thus, in some embodiments, the presently disclosed subject matter is directed to a process for providing a saccharide, the process comprising: providing a plant material comprising intact plant cells; and vacuum extruding the plant material, thereby providing an extruded brei comprising a saccharide. In some embodiments, vacuum extrusion of the plant material comprises reducing the pressure of the plant material by about 3 kPa or more. In some embodiments, the vacuum extrusion comprises reducing the pressure by between about 3 kPa and about 100 kPa. In some embodiments, the plant material is exposed to a vacuum. The vacuum can be between about 90% vacuum up to about a total vacuum. In some embodiments, the vacuum is between about 90% and about 99% vacuum.

In some embodiments, the saccharide comprises a sugar, a starch, or a combination thereof. In some embodiments, the saccharide comprises sucrose.

Plant material that can be used for the presently disclosed process can be derived from a plant selected from the group consisting of a grain, a root, a vegetable, a fruit, a legume, and a grass. In some embodiments, the plant material is derived from a plant including, but not limited to, corn, oats, rice, wheat, barley, millet, cassava, potato, sweet potato, rye, sugar beet (including all Beta vulgaris ssp.), sugar cane, sorghum, sweet sorghum, Jerusalem artichoke, fodder beet, grape, pineapple, apple, pear, peach, and apricot. In some embodiments, the plant material is derived from a sugar beet.

In some embodiments, the plant material further comprises a micro-organism contaminant and vacuum extruding the plant material damages the micro-organism contaminant, thereby providing an extruded brei comprising a reduced amount of micro-organism contaminant than in the original plant material (i.e., prior to vacuum extrusion).

In some embodiments, the process comprises one or more additional steps, wherein the additional steps can comprise the use of one or more enzymes to catalyze the transformation of a sugar, starch, or cellulose molecule present in the decompressed plant material. Such enzyme-catalyzed transformations can comprise hydrolyzing starch or cellulose to form water-soluble oligosaccharides (e.g., dextrins) or sugars, or to further breakdown plant cell walls. In some embodiments, the enzyme-catalyzed transformation can comprise the isomerization of one sugar into another sugar. Additional steps can also comprise the crushing or mashing of the plant material prior to vacuum extrusion. In some cases, the plant material can be heated to a temperature of less than about 100° C. prior to vacuum extrusion.

Any suitable technique can be used to further extract and isolate the desired sugar or starch molecule from the extruded brei. Thus, in some embodiments, the additional steps can comprise separating the liquid and solid phases of the extruded brei. In some embodiments, the additional steps can comprise dissolving sugar or lower molecular weight saccharides (i.e., dextrins) present in the extruded brei into a suitable liquid carrier (e.g., water or an alkaline or acidic aqueous solution) to prepare a saccharide solution, and separating the saccharide solution from undissolved material of the extruded brei. In some embodiments, purification of the desired plant-derived molecule can involve crystallization, sublimination, distillation, and/or liquid, gas, or affinity chromatography.

In some embodiments, the presently disclosed process can comprise providing more (i.e., a higher yield) of a saccharide from a given amount of plant material than would be provided by a conventional process (i.e., a process performed in the absence of a vacuum extrusion transformation).

c. "Betaprocess"

Another aspect of the present invention relates to a multi-step process referred to herein as "Betaprocess" for the subsequent production of ethanol and biogas out of plant material, comprising the steps of a. providing a plant material comprising plant cells as feedstock for said process;
b. subjecting said feedstock to vacuum extrusion;
c. optionally extracting plant substances and/or metabolites other than saccharides (e.g., sugars and/or starch) from the brei;
d. subjecting the complete extruded brei obtained in steps b. or c. above or portions thereof to aerobic fermentation in a batch process or as a continuous process as described hereinabove in a fermentor as described hereinabove to provide a fermented mixture, wherein the fermented mixture comprises ethanol;
e. separating the solid organic matter contained in the fermented mixture obtained in step d. from the liquid phase and separating or isolating ethanol from said liquid phase using a distiller; and
f. using the solid organic matter obtained in step e. as a fuel for anaerobic fermentation in a biogas reactor to produce biogas or as a feed additive for livestock, or as a fertilizer.

The plant substances and/or metabolites extracted in step c. of the method above can be subjected to purification and/or further processing. Such plant substances and/or metabolites comprise, for example, enzymes, proteins, celluloses, hemicelluloses, and/or pectins, but are not limited to those. Methods and apparatuses for the purification and/or further processing of those substances are known to the person skilled in the art.

Further, prior to step d. in the method described above liquefaction and/or saccharification can be accomplished as described hereinabove to degrade the starch and/or dextrins comprised in the brei to produce fermentable sugars.

In addition, the water obtained in step e. can either be used as process water for the preparation of the fermentation mixtures used in step d. or for the preparation of the solid organic matter obtained in step e. to be used as a fuel for the biogas reactor described in step f. Further, the water can be purified for further uses or for re-entering into an environmental or civic water system.

Further, the statements made herein before for each of the single steps of this multi-step process also apply for the multi-step process.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

The following abbreviations are used in the following Examples:

| | |
|---|---|
| ° C. = | degree Celsius |
| ΔP = | change in pressure |
| cfu = | colony forming units |
| $CO_2$ = | carbon dioxide |
| DDG = | dried distiller grain |
| DDGS = | dried distiller grain and solubles |
| DMF = | Dimethylfuran |
| EtOH = | ethanol |
| FAN = | free amino nitrogen |
| g = | gram |
| hl = | hectoliters |
| hr = | hours |
| kg = | kilogram |
| kPa = | kilopascal |
| l = | liters |
| MSG = | monosodium glutamate |
| NIRS = | near-infrared spectroscopy |
| $O_2$ = | oxygen gas |
| SC = | sugar content |
| SLS = | simultaneous liquefaction and saccharification |

The following general materials are used in the following Examples:

PECTINEX™, pectinase enzyme, CELLUBRIX™, cellulose and cellobiase enzyme mix, and ULTRAFLO™ β-glucosidase and xylanase enzyme mix, are commercially available from Novozymes A/S (Bagsvaerd, Denmark). The yeast used was DANSTIL™ 46 EDV yeast available from Lallemand (Lallemand, Inc., Rexdale, Ontario, Canada). AYF™ 1200 yeast nutrient was from Ethanol Technology (Milwaukee, Wis., United States of America).

Example 1

Sugar Beet to Ethanol Production

Sugar beets having 14% sugar content were harvested, defoliated, and stored outdoors. Prior to use, the beets, including beets that were damaged or that had rotted during storage, were pre-washed in a container filled with water. A diagonal auger was inserted into the pre-wash container and served to transport the sugar beets to a conveyor, where stones were picked out. The beets were crushed and subjected to a two-step compression and decompression procedure to disrupt the beet cell walls and provide extruded beet material (i.e., treated brei), which was collected in stainless steel tanks and mixed, as described below, with water, activated yeast, yeast nutriment and, in some cases, one or more enzymes, and fermented. For comparison, beet brei that had not been subjected to the two-step compression and decompression vacuum extrusion procedure (i.e., untreated brei) was also used in two of the fermentation mixtures. This untreated material consisted of sugar beet slices of about 2 mm in size. Following fermentation, the ethanol content of each fermentation mixture was measured and corrected based on the amount of water added to the original treated or untreated beet brei to reflect the volume percentage of ethanol that had been produced based on the volume of the original brei.

Chemical analysis was performed using NIRS. Microbiological testing was performed to measure the amount of bacteria present in the brei both before and after vacuum extrusion.

Mixture 1: Fermentation mixture content=400 kg treated brei, 6.25% (by volume) water, yeast nutrient (20 g/hl), activated yeast (6%), no additional enzymes. Fermentation carried out at 33° C. for 72 hours. Ethanol content (measured)= 9.97%; ethanol content (corrected)=10.6%.

Mixture 2: Fermentation mixture content=400 kg treated brei, 6.25% (by volume) water, PEKTINEX™ (60 g/100 kg brei), CELLUBRIX™ (50 g/100 kg brei); ULTRAFLO™ (20 g/100 kg brei), yeast nutrient (20 g/hl), activated yeast (6%). Fermentation carried out at 33° C. for 48 hours. Ethanol content (measured)=9.32%; ethanol content (corrected)= 9.9%.

Mixture 3: Fermentation mixture content=400 kg treated brei, 6.25% (by volume) water, PEKTINEX™ (60 g/100 kg brei), CELLUBRIX™ (50 g/100 kg brei); ULTRAFLO™ (20 g/100 kg brei), yeast nutrient (20 g/hl), activated yeast (6%). Fermentation carried out at 25° C. for 72 hours. Ethanol content (measured)=8.87%; ethanol content (corrected)= 9.5%.

Mixture 4: Fermentation mixture content=400 kg treated brei, 6.25% (by volume) water, PEKTINEX™ (60 g/100 kg brei), CELLUBRIX™ (50 g/100 kg brei); ULTRAFLO™ (20 g/100 kg brei), yeast nutrient (20 g/hl), activated yeast (6%). Fermentation carried out at 33° C. for 48 hours. Ethanol content (measured)=9.32%; ethanol content (corrected)= 9.8%.

Mixture 5: Fermentation mixture content=400 kg untreated brei, 6.25% (by volume) water, PEKTINEX™ (60 g/100 kg brei), CELLUBRIX™ (50 g/100 kg brei); ULTRAFLO™ (20 g/100 kg brei), yeast nutrient (20 g/hl), activated yeast (6%). Fermentation carried out at 25° C. for 96 hours. Ethanol content (measured)=8.43%; ethanol content (corrected)=9.0%.

Mixture 6: Fermentation mixture content=400 kg untreated brei, 6.25% (by volume) water, PEKTINEX™ (60 g/100 kg brei), CELLUBRIX™ (50 g/100 kg brei); ULTRAFLO™ (20 g/100 kg brei), yeast nutrient (20 g/hl), activated yeast (6%). Fermentation carried out at 33° C. for 72 hours. Ethanol content (measured)=8.3%; ethanol content (corrected)=9.3%.

Mixture 7: Fermentation mixture content=120 kg treated brei, 35% (by volume) water, PEKTINEX™ (60 g/100 kg brei), CELLUBRIX™ (50 g/100 kg brei); ULTRAFLO™ (20 g/100 kg brei), yeast nutrient (20 g/hl), activated yeast (6%). Fermentation carried out at 35° C. for 10 hours. Ethanol content (measured)=6.2%; ethanol content (corrected)= 9.5%.

Mixture 8: Fermentation mixture content=7000 kg treated brei, 15% (by volume) water, PEKTINEX™ (25 g/100 kg brei) as the only enzyme, yeast nutrient (20 g/hl), rehydrated yeast. Fermentation carried out at 35° C. for 48 hours. Ethanol content (measured)=8.13%; ethanol content (corrected)= 9.5%.

Example 2

Results of Sugar Beet to Ethanol Production

The fermentation conditions and ethanol content produced in fermentation mixtures 1-8 described in Example 1 are shown in Table 1 below.

The ethanol yield from vacuum-treated sugar beet brei fermented at a temperature between 33-35° C. was between 9.5 and 10.6%. At fermentation temperatures above 33° C., 90% of the ethanol was produced within the first 20 hours. Treated sugar beet brei fermented at 25° C. resulted in a 0.5% by volume reduction in ethanol production. As shown by the results from mixture 1, ethanol yield is not negatively influenced by a lack of enzymes, although the use of at least 25 g/hl PECTINEX™ pectinase enzyme, served to liquefy the brei, making it easier to ferment and to simplify handling.

Compared to the treated beet brei, sugar beet brei that had not been transformed using vacuum extrusion generated lower ethanol yields (see mixtures 5 and 6) of 9.0% at a fermentation temperature of 25° C. and 9.3% at a fermentation temperature of 33° C.

TABLE 1

Ethanol content of fermented Sugar Beet brei.

| Mixture | Fermentation Temp. (° C.) | Fermentation Duration (h) | EtOH % (by volume) | EtOH % (corrected) |
|---|---|---|---|---|
| 1 (no enzymes) | 33 | 72 | 9.97 | 10.6 |
| 2 | 33 | 48 | 9.32 | 9.9 |
| 3 | 25 | 72 | 8.87 | 9.5 |
| 4 | 33 | 48 | 9.32 | 9.8 |
| 5 (Untreated brei) | 25 | 96 | 8.43 | 9.0 |

TABLE 1-continued

Ethanol content of fermented Sugar Beet brei.

| Mixture | Fermentation Temp. (° C.) | Fermentation Duration (h) | EtOH % (by volume) | EtOH % (corrected) |
|---|---|---|---|---|
| 6 (Untreated brei) | 33 | 72 | 8.3 | 9.3 |
| 7 (35% water) | 35 | 10 | 6.2 | 9.5 |
| 8 (15% water, PECTINEX ™ only) | 35 | 48 | 8.13 | 9.5 |

No positive effect based on the ethanol yield could be observed for Sugar beet plant material subjected to compression prior to decompression compared to Sugar beet plant material only subjected to decompression. The ethanol yields are comparable for the two-step compression and decompression procedure according to the present invention and the decompression procedure according to the present invention.

Example 3

Comparison of Ethanol Yield from a Conventional Process to Ethanol Yield from a Vacuum Extrusion Process Theoretical yield of Ethanol from Sugar Beet: One ton of sugar beets having a sugar content of 14% contains 140 kg of sugar.

The conversion of glucose to ethanol can be expressed by the equation:

180 g of glucose=92 g EtOH+88 g CO2+23.5 calories; which gives a sugar to ethanol conversion factor of 0.51. The specific density of EtOH is 1.25 g/L. Thus, the potential or theoretical EtOH yield after fermentation of all available sugar in one ton of sugar beets having 14% sugar content would be 71.4 kg (89.25 liters) of EtOH.

Conventional Juice Extraction Process (as used in a beet-sugar factory with sliced sugar beet and hot water diffusion): The raw sugar beet juice after traditional extraction processes contains about 90% of the total initially available sugar, giving 126 kg of available sugar for fermentation. Based on the sugar to ethanol conversion factor of 0.51, 126 kg of sugar can provide 64.26 kg (80.325 liters) of EtOH.

Vacuum Extrusion Process: Based on the fermentation trials described in Example 1, the average yield of ethanol from the fermentation of sugar beet feedstock pre-treated by a two-step compression/decompression vacuum extrusion is 9.6% (based on the volume of undiluted beet brei). At this level of conversion, 1 ton of treated sugar beets can yield 95.6 liters of EtOH.

Accordingly, the ratio of ethanol that can be produced from the vacuum extrusion-comprising process to that which is calculated to be produced from a conventional juice extraction process is 95.6 liters/80.325 liters, which is a ratio of 1.19. This indicates that the plant-to-ethanol process comprising vacuum extrusion yields 19% more ethanol compared to the traditional process. Further, as the amount of ethanol produced is higher than the theoretical amount based on the available sugar content, it appears that other molecules from the plant cell, in addition to the sugar, are being transformed and fermented into ethanol. Finally, using a higher sugar content beet, such as beet comprising 17% sugar content, the presently disclosed process is expected to yield 116 liters of EtOH from one ton of plant material.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of producing a biofuel, the method comprising:
a) compressing sugar beet plant material to provide a compressed plant material;
b) vacuum extruding the compressed plant material wherein the vacuum extruding comprises subjecting the compressed plant material to a reduction in pressure of between about 3 kPa to about 100 kPa to produce an extruded brei;
c) fermenting the extruded brei of b) to provide a fermented mixture; and
d) producing said biofuel, wherein the biofuel is ethanol, wherein at least about 19% to about 25% more ethanol is produced compared to conventional sugar beet plant-to-ethanol processes, wherein the conventional plant-to-ethanol process is performed in the absence of a vacuum extruding step.

2. The method of claim 1, wherein the vacuum extruding of b) comprises introducing the compressed plant material of a) to a vacuum chamber and operating the vacuum chamber at between about 90% and about 99% vacuum.

3. The method of claim 1, wherein the sugar beet plant material of a) is mashed or crushed.

4. The method of claim 1, wherein the sugar beet plant material of a) is heated to between about 70° C. to about 90° C.

5. The method of claim 1, wherein ethanol by volume is at least 9.5%, calculated based on the volume of the extruded brei.

6. The method of claim 1, wherein the fermented mixture of c) is subjected to distillation to separate the ethanol from the fermented mixture, thereby providing a residual fermented mixture.

7. The method of claim 6, wherein the residual fermented mixture is introduced into a biogas reactor.

8. The method of claim 7, wherein the distillation is performed using energy produced from a biogas reactor.

* * * * *